United States Patent [19]
Farone et al.

[11] Patent Number: 5,820,687
[45] Date of Patent: *Oct. 13, 1998

[54] METHOD OF SEPARATING ACIDS AND SUGARS USING ION RESIN SEPARATION

[75] Inventors: William A. Farone, Irvine; John E. Cuzens, Santa Ana, both of Calif.

[73] Assignee: Arkenol, Inc., Las Vegas, Nev.

[ * ] Notice: The term of this patent shall not extend beyond the expiration date of Pat. No. 5,580,389.

[21] Appl. No.: 664,184

[22] Filed: Jun. 13, 1996

Related U.S. Application Data

[60] Continuation of Ser. No. 465,855, Jun. 6, 1995, Pat. No. 5,580,389, which is a division of Ser. No. 38,628, Mar. 26, 1993, Pat. No. 5,562,777.

[51] Int. Cl.$^6$ .............. C13D 3/14; B01D 15/04; C07H 1/00; C12P 19/02
[52] U.S. Cl. .............. 127/46.2; 127/36; 127/37; 127/46.3; 435/99; 435/100; 435/105; 435/803; 536/1.1; 536/124; 536/127; 210/665; 210/673
[58] Field of Search .................. 127/36, 37, 46.2, 127/46.3; 435/100, 105, 99, 803; 536/1.1, 124, 127; 210/665, 673

[56] References Cited

U.S. PATENT DOCUMENTS

| | | | |
|---|---|---|---|
| 4,242,455 | 12/1980 | Muller et al. | 435/162 |
| 4,612,286 | 9/1986 | Sherman et al. | 435/157 |
| 4,742,814 | 5/1988 | Sinner et al. | 127/37 |
| 4,880,473 | 11/1989 | Scott et al. | 127/37 |
| 5,084,104 | 1/1992 | Heikkila et al. | 127/46.2 |
| 5,188,673 | 2/1993 | Clausen et al. . | |
| 5,407,580 | 4/1995 | Hester et al. | 127/46.3 |
| 5,538,637 | 7/1996 | Hester et al. | 127/46.3 |
| 5,560,827 | 10/1996 | Hester et al. | 127/46.3 |
| 5,580,389 | 12/1996 | Farone et al. | 127/46.3 |
| 5,597,714 | 1/1997 | Farone et al. | 127/46.3 |

FOREIGN PATENT DOCUMENTS

| | | | |
|---|---|---|---|
| 859449 | 8/1981 | U.S.S.R. | 127/37 |

OTHER PUBLICATIONS

"Integrated Fuel Alcohol Production Systems, Phase III" Barrier, et al., Experimental Facility Testing Report for Jan. 15, 1985—Jan. 15, 1986.

"Process Considerations for Scale–up of Liquid Chromatography and Electrophoresis" Rudge, et al., *Separation, Recovery, and Purification in Biotechnology*, pp. 122–152 (1986).

"Application of Continuos Substrate Feeding to the ABE Fermentation: Relief of Product Inhibition Using Extraction, Perstraction, Stripping, and Pervaporation". Qureshi, et al., *Biotechnology Prog.*, 8: No. 5, pp. 382–390 (1992).

"Concentrated Sulfuric Acid Processes" Fan, et al., *Cellulose Hydrolysis*, Section 5.2.2, pp. 170–172 (Date unknown).

"Conversion of Cotton Trash and Other Residues to Liquid Fuel" Broder, et al., pp. 189–200 (Publication and date unknown).

"Ethanol from Biomass by Concentrated Acid Hydrolysis and Fermentation" Clausen, Ph.D., et al., pp. 1319–1342 (Publication and date unknown).

*Primary Examiner*—Glenn Caldarola
*Assistant Examiner*—Patricia L. Hailey
*Attorney, Agent, or Firm*—Knobbe Martens; Olson & Bear, LLP

[57] ABSTRACT

A economically viable method for producing sugars using concentrated acid hydrolysis of biomass containing cellulose and hemicellulose is disclosed. The cellulose and hemicellulose in the biomass is first decrystallized and then hydrolyzed to produce a hydrolysate containing both sugars and acid. Silica present in the biomass can then be removed for further processing. The remaining solids are then subjected to a second decrystallization and hydrolyzation to optimize the sugar yields. An improved method for separating the sugars from the acid in the hydrolysate is also disclosed. The resulting sugar stream can then be fermented, using an improved method which allows both hexose and pentose sugars to be fermented simultaneously.

12 Claims, 3 Drawing Sheets

METHOD OF SEPARATING ACIDS AND SUGARS USING ION RESIN SEPARATION

RELATED APPLICATIONS

This application is a continuation of U.S. patent application Ser. No. 08/465,855, filed Jun. 6, 1995, now U.S. Pat. No. 5,580,389, which is a divisional of U.S. patent application Ser. No. 08/038,628, filed Mar. 26, 1993, now U.S. Pat. No. 5,562,777.

FIELD OF THE INVENTION

The present invention relates to a process for hydrolysing biomass, and, more specifically, to a process for producing sugars through concentrated sulfuric acid hydrolysis of materials containing cellulose and hemicellulose.

BACKGROUND OF THE INVENTION

Cellulose comprises the major part of all plant biomass. The source of all cellulose is the structural tissue of plants. It occurs in close association with hemicellulose and lignin, which together comprise the major components of plant fiber cells. Cellulose consists of long chains of beta glucosidic residues linked through the 1,4 positions. These linkages cause the cellulose to have a high crystallinity and thus a low accessibility to enzymes or acid catalysts. Hemicellulose is an amorphous hetero-polymer which is easily hydrolyzed. Lignin, an aromatic three-dimensional polymer, is interspersed among the cellulose and hemicellulose within the plant fiber cell.

It has been estimated that about three quarters of the approximately 24 million tons of biomass generated on cultivated lands and grasslands is waste. The utilization of such waste materials for developing alternate sources of fuels, chemicals and other useful products has long been desired. However, attempts to hydrolyze cellulose have not yet succeeded in providing an economically viable method for producing high yields of sugars, due primarily to the crystalline structure of cellulose and the presence of lignin therein.

Previously reported processes for hydrolysing cellulose include biological and non-biological means of depolymerization. The biological methods involve the use a cellulase enzyme. The oldest and best known non-biological method of producing sugars from cellulose is the use of acid hydrolysis. The acid most commonly used in this process is sulfuric acid. In general, sulfuric acid hydrolysis can be categorized as either dilute acid hydrolysis or concentrated acid hydrolysis.

The dilute acid processes generally involve the use of 0.5% to 15% sulfuric acid to hydrolyze the cellulosic material. In addition, temperatures ranging from 90°–600° Celsius, and pressure up to 800 psi are necessary to effect the hydrolysis. At high temperatures, the sugars degrade to form furfural and other undesirable by-products. The resulting glucose yields are generally low, less than 50%. Accordingly, the dilute acid processes have not been successful in obtaining sugars from cellulosic material in high yields at low cost.

The concentrated acid processes have been somewhat more successful, producing higher yields of sugar. These processes typically involve the use of 60% to 90% sulfuric acid to effect hydrolysis. These processes, although successful at producing sugar yields above 90%, have not been implemented commercially in the past due to the high cost of concentrated sulfuric acid and its subsequent recovery, the difficulties encountered in handling concentrated sulfuric acid, and the need for equipment resistant to the acid at high temperatures. In addition, the higher the acid concentration used, the more energy required to concentrate the acid, resulting in these processes being economically disadvantageous.

More recently, however, the concentrated acid hydrolysis process has become the focus of additional research. (See L. T. Fan, M. M. Gharpuray and Y. H. Lee, Cellulose Hydrolysis, p. 170–172, 1992 and J. D. Broder, J. W. Barrier and G. R. Lightsey, "Conversion of Cotton Trash and Other Residues to Liquid Fuel", presented at the Conference of the American Society of Agricultural Engineers, Dec. 14–15, 1992.) Such processes generally consist of the following stages: (1) prehydrolysis to hydrolyze the hemicellulose portion, (2) main hydrolysis to hydrolyze the cellulose, and (3) post hydrolysis to form glucose from oligosaccharides formed in step (2). The first step involves the addition of sulfuric acid to the biomass which is then heated to at least 100° C. to break down the hemicellulose. The result of this prehydrolysis step is a solution containing not only virtually all of the $C_5$ sugars, but also $C_6$ sugars. These $C_6$ sugars are thus not recovered if the $C_5$ sugar stream is not utilized, resulting in lower sugar yields. After the sugar stream produced by the prehydrolysis step is removed, concentrated acid is added to disrupt the crystalline lattice of the cellulose and form glucose. The sugars produced are then fermented to alcohols. It has been recognized, however, that in order to commercialize such a process, the steps must be simplified, the energy consumption reduced, and the difficulties encountered in recycling spent acids eliminated.

Additional problems faced in the commercialization of known acid hydrolysis processes include the production of large amounts of gypsum when the spent or used acid is neutralized. The low sugar concentrations resulting from the processes require the need for concentration before fermentation can proceed. When hydrolysis is carried out at temperatures above 150° C., compounds such as furfural are produced from the degradation of pentoses. These compounds inhibit fermentation, and some are toxic.

In addition to these difficulties, it has been recognized that the fermentation of the sugars produced by concentrated acid hydrolysis presents additional problems. The hydrolysis of cellulose and hemicellulose results in the production of both $C_5$ and $C_6$ sugars. The hexose sugars are known to ferment easily, while the pentose sugars are generally more difficult to ferment. Thus, the resulting sugars must first be separated, which often involves the use of complicated separation techniques, and then fermented by different microorganisms known to ferment either hexose or pentose sugars alone.

Previous acid hydrolysis processes have not taken into account how biomass containing high amounts of silica are to be treated. Disposal of the silica poses a potential environmental and economic liability. In projects that use biomass to generate energy by combustion, high silica means high slagging tendency, as well as problems with handling large quantities of ash produced when the biomass is burned.

Yet silicon compounds are of great commercial importance, and the recovery of silica from agricultural waste has become increasingly important. (See A. Karera, S. Nargis, S. Patel and M. Patel, "Silicon Based Materials from Rice Husk", Journal of Scientific & Industrial Research, Vol. 45, 1986, pp. 441–448.) It is well known that treatment of the biomass with sodium hydroxide will dissolve cellulose and hemicellulose, allowing their separation from the lignin.

However, small chain cellulosics often contaminate the silica product during the removal process, thus lowering the sugar yield. In addition, the removal of the silica, done by filtration, is hampered by the formation of a thick gel which is very difficult to filter.

Thus, there is an urgent need for an economically viable, environmentally safe process for producing sugars from biomass containing cellulose and hemicellulose.

SUMMARY OF THE INVENTION

According to one aspect, the present invention provides a method for producing sugars from materials containing cellulose and hemicellulose. The method involves mixing the biomass with a solution of between 25% and 90% acid, and more preferably, between 70% and 77%, to effect decrystallization of the cellulose and hemicellulose. In a preferred embodiment, the acid solution is added to achieve a ratio of pure acid to cellulosic and hemicellulosic material of at least 1:1. More preferably, the ratio achieved is 1.25:1. The acid used in the preferred embodiment of the invention is sulfuric acid.

According to another aspect of the present invention, hydrolysis of the cellulosic and hemicellulosic materials is achieved by diluting the acid to a concentration of between 20% and 30%, and heating the mixture. Preferably, the mixture is heated to a temperature of between 80°–100° C. for between 40 and 480 minutes, and the hydrolysis is performed at atmospheric pressure. The hydrolysate is then separated from the solid materials, preferably through the pressing of the hydrolyzed biomass. The liquid hydrolysate which contains sugars and acid is collected for further processing.

In a preferred embodiment of the present invention, the raw materials are first washed to remove dirt and contamination. The materials are then optionally dried, preferably to a moisture content of about 10%. The raw materials can then be commuted to particles, preferably of a size of between 0.075 mm and 7 mm, and more preferably to an average size of about 5 mm before decrystallization. This commuting can be done by any of a number of means, including grinding, chopping and hammermilling.

According to another aspect of the present invention, the decrystallization and hydrolysis of the raw materials are repeated. The solid material separated after the first hydrolysis is mixed with a solution of 25–90% sulfuric acid, and more preferably, between 70% and 77% sulfuric acid, thereby further decrystallizing the remaining solid material. In the preferred embodiment, the acid solution is added to achieve a ratio of pure acid to cellulosic and hemicellulosic material of at least 1:1. More preferably, the ratio achieved is 1.25:1.

To effect a second hydrolysis, another aspect of the present invention, the acid is then diluted to a concentration of between 20% and 30%, and the mixture is heated thereby further hydrolyzing cellulose and any remaining hemicellulose. Preferably, the mixture is heated to a temperature of between 80°–100° C. for between 40 and 480 minutes, and the hydrolysis is performed at atmospheric pressure. The hydrolysate is then separated, again preferably by pressing the hydrolyzed biomass. The liquid hydrolysate is collected and preferably mixed with the first hydrolysate for further processing, while the remaining solid material may be optionally pelletized for fuel.

Another aspect of the present invention provides an improved method for separating the sugars from the acid in the hydrolysate to produce a liquid containing a total of at least 15% sugar which is not more than 3% acid. This method involves the use of a resin separation unit wherein the sugars are adsorbed on a strong acid resin. The resin separation unit is preferably a cross-linked polystyrene cation exchange resin bed, wherein the resin is cross linked with divinylbenzene and treated with sulfuric acid to produce a strong acid resin. Preferably, the divinylbenzene is at a concentration of from about 6% to about 8%. Alternatively, this resin can be formed by polymerizing vinylbenzyl chloride with divinylbenzene and treating with sodium sulfite to produce a strong acid resin. Again, preferably the divinylbenzene is at a concentration of from about 6% to about 8%.

The preferred form of the resin used in the separation step is beads having a diameter of from about 200 to about 500 micrometers. Preferably, the resin bed has a flow rate of from about 2 to about 5 meters per hour and is heated to a temperature of 40°–60° C. In the preferred embodiment, the resin bed has a tapped bed density of 0.6 g/ml to 0.9 g/ml and the resin has a strong acid capacity of at least 2 meq/g.

In a preferred embodiment, the hydrolysate is added to the resin bed, and the sugars are adsorbed onto the resin. The resin is then purged with a gas substantially free of oxygen, which pushes the acid out of the resin before the washing step. This washing step comprises washing the resin with water substantially free of oxygen, thereby producing a sugar stream containing at least 98% of the sugar present in the hydrolysate added to the separation unit.

In yet another aspect of the present invention, after the separation of the acid from the sugar stream, the acid is preferably concentrated for reuse. This concentration preferably is in the form of evaporation.

In still another aspect of the present invention, there is provided an improved method for fermenting the sugars produced by the concentrated acid hydrolysis of cellulosic and hemicellulosic materials to form an alcohol. The fermentation process comprises adjusting the pH of the sugar stream to neutralize any remaining acid and to remove metal ions. Preferably, the pH is adjusted by adding a base such as calcium hydroxide or calcium oxide until the pH reaches about 11, and then back titrating with acid to a pH of about 4.5. Nutrients such as magnesium, nitrogen, potassium phosphate, trace metals and vitamins are then added to allow growth of microbial organisms. The sugar solution is then mixed with a microbial organism known to produce useful fermentation products. These useful fermentation products include ethanol, n-butanol, isopropyl alcohol, acetic acid, glycerol, butyric acid, lactic acid, 2,3-butandiol, propionic acid, itaconic acid, citric acid, fumaric acid and acetone.

The fermentation process of the present invention further comprises allowing the fermentation to proceed for 3–5 days, while preferably continuously removing volatile fermentation products by recirculating carbon dioxide through a cooled condensing column. After 3–5 days, the fermentation products are collected from the condensing column and distilled. The yeast are separated from the fermentation products, preferably through centrifugation, and can be recycled for reuse.

The microorganisms used in the fermentation process of the present invention can be, for example, a yeast such as *Candida kefyr, Pichia stipitis,* respiratory deficient strains of *Saccharomyces cerevisiae, Hansenula anomala, Hansenula jadinii, Hansenula fabianii* and *Pachysolen tannophilus*. These yeast are preferably grown on pentose solutions for about 1 to 2 weeks prior to their use in the fermentation process. Alternatively, the microorganism can be a bacteria such as Clostridium species, Acetobacter species, Lactobacillus species, Aspergillis species, Propionibacteria species and *Zymomonas mobilis*.

Yet another aspect of the present invention provides a method for removing and processing silica from biomass such as rice straw and cotton gin trash which contain high amounts of silica. This method involves treating the solid material remaining after the first hydrolysis with sodium hydroxide, preferably at a concentration of between 5% and 10%, to produce an extract. The pH of the extract is then reduced to about 10, preferably through the addition of an acid such as hydrochloric acid or sulfuric acid. This results in the precipitation of silicic acid. The silicic acid is then removed, preferably by filtering. The silicic acid may then be treated with an oxidizing agent such as NaOCl, to reduce the color of the silicic acid. The silicic acid can be further processed into silica gel, sodium silicate and potassium silicate. The remaining extract is then preferably recycled by adding NaOH to a final concentration of between 5% and 10%, and then adding the extract to new solids prior to the treatment of these solids with sodium hydroxide.

Further aspects of the present invention will become apparent to those of ordinary skill in the art upon reference to the ensuing description of the invention.

DETAILED DESCRIPTION OF THE INVENTION

Introduction

This invention provides an improved process for producing sugars from biomass containing cellulose and hemicellulose using concentrated sulfuric acid. The sugars produced can be used as animal or human food, as feedstock chemicals to make sugar derivatives such as sugar esters, or as feedstock for fermentation to ethanol or other products such as butanol, propanol, acetone, ethyl acetate, and many other chemicals for which specific microorganisms can be used to follow a specific metabolic pathway.

The process of the present invention provides a means for producing sugars from biomass which also reduces the amount of waste product or effluents produced. The process is designed to reuse all aqueous streams and to convert all solids to saleable or useful products. Much of the acid used is recovered for recycle. In the case where the biomass contains high levels of silica, the process is able to produce silica gel, sodium silicate, or potassium silicate as ancillary products. In the portions of the process involving fermentation, the fermentation of both the $C_5$ and $C_6$ sugars can be accomplished simultaneously using naturally occurring microorganisms. In addition, a high yield of sugar is obtained from the hydrolysis of the biomass, making concentration of the sugar streams prior to fermentation unnecessary.

Other features of the present invention that contribute to its efficiency and economic feasibility include the use of atmospheric pressure and relatively low temperatures. The process does not result in the production of furfural and similar undesirable by-products which are toxic and inhibit fermentation. The process of the present invention does not require the use of exotic and expensive materials of construction such as tantalum steel.

As will be explained more fully below, the process of the present invention provides an efficient, cost-effective means of producing useful chemicals from the hydrolysis of agricultural waste, while at the same time producing little or no waste effluents or materials.

The examples which follow are illustrative of the process of the present invention.

Decrystallization

Figure 1:
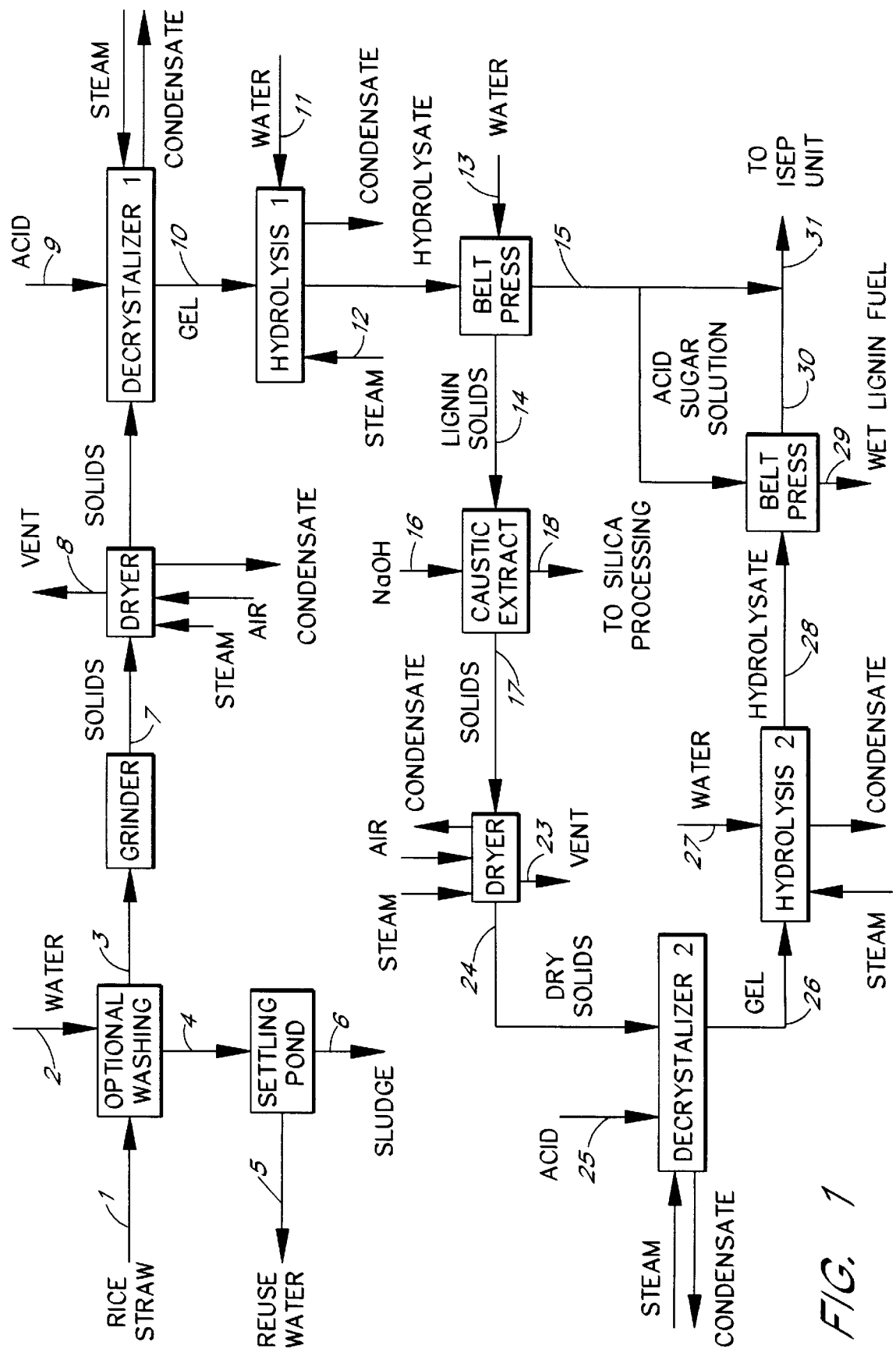
FIG. 1 is a schematic view of the method of the present invention, illustrating the decrystallization and hydrolysis stages.

The raw materials used in the method of the present invention are blended such that the cellulose and hemicellulose content is at least 65%, and more preferably about 75%. As an optional first step in the process, the biomass can be washed to remove gross dirt and contamination. As seen in FIG. 1, the rice straw 1, the biomass used as an example throughout the figures, is washed with water 2. Advantageously, the method of the present invention can be used with a variety of raw materials, including rice straw, which, because of its high silica content, is more difficult to process than other materials. It should be noted, however, that the principles of the present invention are not limited to any particular type of biomass, but are intended to apply to a broad range of materials. Rice straw is intended to be merely exemplary in nature.

After the washing is complete, the used water is transferred to a settling pond 4, to allow dirt and other sediment to collect on the bottom 6, after which the water can be reused 5 to wash the next portion of rice straw before processing.

Once the rice straw has been cleaned, it may be optionally dried 8, preferably to a moisture content of approximately 10%. After drying, the material is ground 7 to particles ranging in size from 0.075 mm to 7 mm. Preferably, the particles range in size from 3 mm to 7 mm, and are of an average size of 5 mm. It should be noted that for some materials the order of these two steps should be reversed. That is, the material may be wet ground using a device such as a hydropulper and then dried.

The rice straw is now ready for the decrystallization stage. In the process of the present invention, raw materials containing cellulose and/or hemicellulose are first mixed with concentrated sulfuric acid 9 at a concentration of between 25% and 90% to effect decrystallization. Preferably, the concentration of acid used is between 70% and 77%. The acid should be added to achieve a ratio of the weight of pure acid to the weight of cellulosic and hemicellulosic materials of at least 1:1. Preferably, the ratio achieved is 1.25:1. The addition of acid to the biomass results in the formation of a thick gel 10. Advantageously, this mixture of the raw material with the acid results in the disruption of the bonds between the cellulose and hemicellulose chains, making the long chain cellulose available for hydrolysis.

The decrystallization is performed such that the temperature does not exceed 80° C., and is preferably in the range of 60°–80° C. If the temperature during decrystallization exceeds 80° C., much of the $C_5$ sugars will be lost in the subsequent hydrolysis. The method of the present invention uses conditions which conserve the more reactive sugars that are produced earlier in the hydrolysis process. The decrystallization step prevents premature hydrolysis and consequently increased degradation of the sugars. The decrystallization stage is further described in Examples 1–3 which follow.

EXAMPLE 1

Rice straw, containing 75% by weight of cellulose plus hemicellulose, and weighing 50.01 grams was mixed with 66.82 grams of 77% $H_2SO_4$. The rice straw was slowly added to the $H_2SO_4$ such that there was excess liquid available after each increment was added. The temperature was kept below 80° C. After the last amount of rice straw was added the resulting gelatinous mass was thoroughly mixed.

EXAMPLE 2

Rice straw weighing 50.04 grams was mixed with 98.91 grams of 77% $H_2SO_4$. The rice straw was slowly added to the $H_2SO_4$ such that there was excess liquid available after each increment was added. The temperature was kept below 80° C. After the last amount of rice straw was added the resulting gelatinous mass was thoroughly mixed.

EXAMPLE 3

A mixture of wood prunings and newspaper weighing 100.00 grams was mixed with 167.63 grams of 77% $H_2SO_4$. The wood prunings were ground to 3–7 mm in size and 40 grams were mixed with 60 grams of the newspaper which had been shredded into approximately 6 mm pieces. The mixture was slowly added to the $H_2SO_4$ such that there was excess liquid available after each increment was added. The temperature was kept below 80° C. After the last amount of prunings and newspaper was added the resulting gelatinous mixture was thoroughly mixed.

First Hydrolysis

After the decrystallization stage, the concentrated acid in the mixture is diluted, preferably to a concentration of between 20% and 30%, and preferably using recycled water 11. The mixture is then heated to a temperature of between 80° and 100° Celsius to effect hydrolysis 12. The hydrolysis is allowed to continue for between 40 and 480 minutes, depending on the temperature and the concentration of cellulose and hemicellulose in the raw materials. If the proper time is exceeded, the rate of degradation of the hexoses and pentoses will exceed their rate of formation. Thus, to increase the sugar yield, it is important to stop the first hydrolysis after a time and remove the sugars, then perform a second hydrolysis to convert the remainder of the cellulose and hemicellulose to sugars. After hydrolysis, the acid sugar solution is separated from the remaining solids, preferably by pressing 15. The hydrolysis stage is further described in Examples 4–6 below.

EXAMPLE 4

To the resulting gelatinous mass from Example 1, 54.67 grams of water were added for hydrolysis to reduce the acid concentration of the total mixture to 30%. The sample was heated to 100° C. for 60 minutes. Some water evaporation occurred during the heating. The gelatinous mass was pressed to yield 93 grams of a liquid which was 17.1% sugars and 35.52% acid.

EXAMPLE 5

After the resulting gelatinous mass in Example 2 was thoroughly mixed, 104.56 grams of water were added to reduce the acid concentration of the total mixture to 30%. The sample was heated to 100° C. for 60 minutes. The gelatinous mass was pressed to yield 188.9 grams of a liquid which was 16.5% sugars and 34.23% acid.

EXAMPLE 6

After the resulting gelatinous mass from Example 3 had been thoroughly mixed, 162.62 grams of water were added for hydrolysis to reduce the acid concentration of the total mixture to 30%. The sample was heated to 100° C. for 60 minutes. Some water evaporation occurred during the heating. The gelatinous mass was pressed to yield 214.3 grams of a liquid which was 17.6% sugars and 36.85% acid.

After pressing, the resulting cake containing the solid matter was washed with 170 grams of water and pressed again to yield a liquid which was 16.3% acid and 8.92% sugar, which was used for subsequent washing to increase the sugar yield.

Silica Processing

Figure 3:
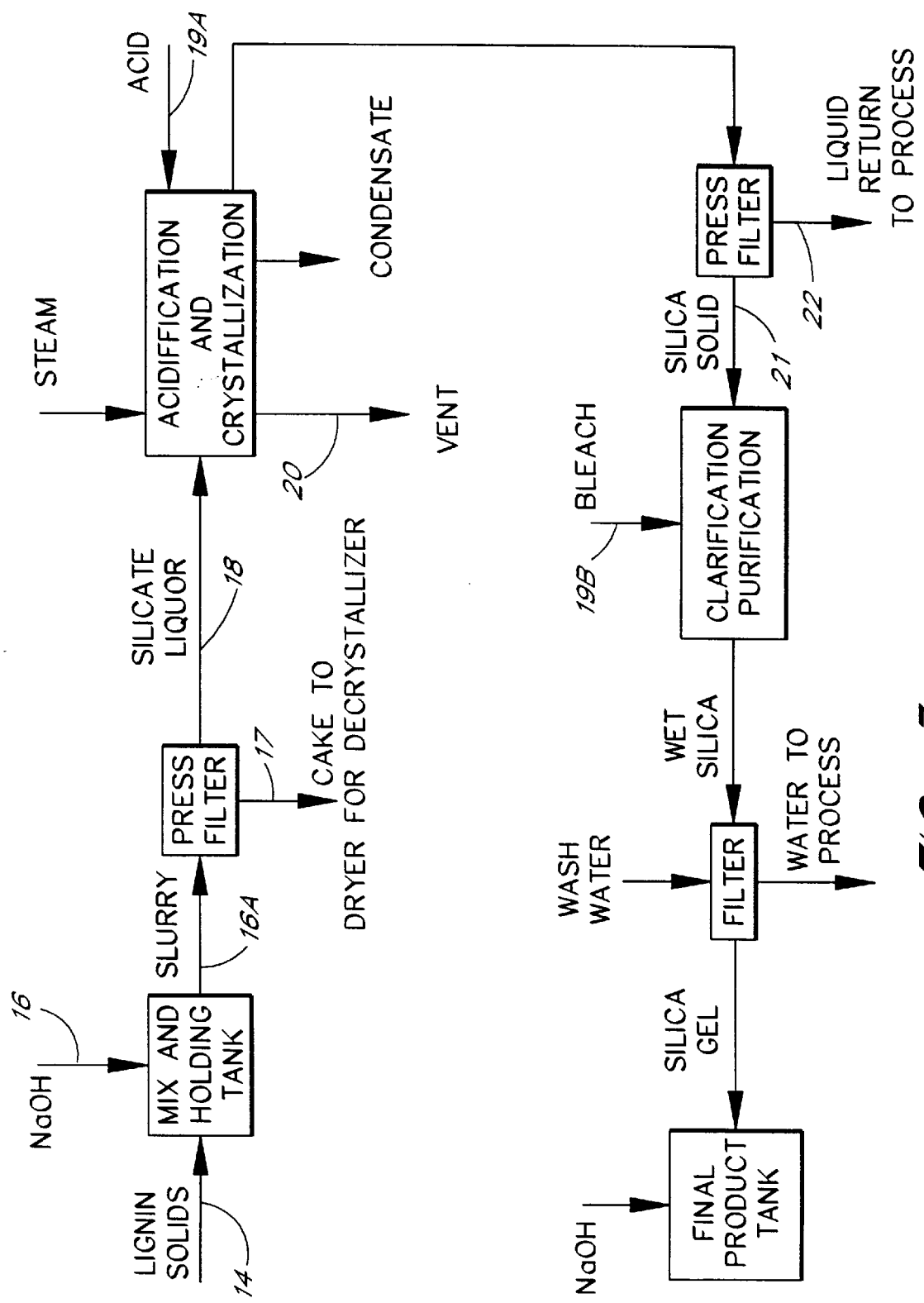
FIG. 3 is a schematic view of the method of the present invention, illustrating the silica processing stages.

The present invention advantageously also provides for the treatment of materials containing high amounts of silica. This process is illustrated in FIG. 3. The pressed solids 14 remaining after the first hydrolysis can be treated with 5%–10% sodium hydroxide 16 to extract silicic acid 18. This stage of the process is optional, and is used when the biomass contains high amounts of silica, such as is the case with rice straw and cotton gin trash. After treatment with sodium hydroxide 16 the solids are first heated 16A and then pressed 17 and washed with water to extract a liquid 18. This liquid is treated with acid 19A to reduce the pH, creating a precipitate 21 which is separated, preferably by filtration 22. The material in the filter is bleached 19B to produce a material which is essentially pure silica gel. This silica gel can be further treated to produce sodium silicate, potassium silicate, or other useful materials. The extraction of silica is further described in connection with Examples 7–9 below.

EXAMPLE 7

Rice straw hydrolysis cake, formed as in Example 1 above, weighing 499.75 grams after pressing out the sugar hydrolysate was treated with 659.8 grams of 5% NaOH solution. The mixture was heated to 80° C. for 90 minutes. The cake was pressed and washed with water. The total liquid extracted was found to have a pH above 12. The liquid was treated with concentrated HCl to reduce the pH to 10. A light fluffy precipitate formed which was separated by filtration. The material was bleached in the filter by addition of 11% solution of NaOCl to produce an off-white material which is essentially pure silica gel. The material from the filter was recovered as silica by drying to the desired moisture level.

EXAMPLE 8

The filter cake silica gel prepared by the method of Example 7 was treated with NaOH pellets to produce sodium silicate. Analysis of the sodium silicate solution by FT-IR spectroscopy showed recovery of the silica from the cake to be greater than 85%.

EXAMPLE 9

The filter cake silica gel prepared by the method of Example 7 was treated with KOH pellets to produce potassium silicate in quantitative yields.

Second Decrystallization and Hydrolysis

To increase the sugar yields produced using the method of the present invention, yet another aspect of the present invention involves a second decrystallization and hydrolysis step. The solids remaining after the first hydrolysis, or alternatively, the solids remaining after treatment with sodium hydroxide to extract silica, are dried 23. The dry solids 24 are mixed with concentrated sulfuric acid 25 at a concentration of between 25% and 90% to effect the second decrystallization. Preferably, the acid concentration is between 70% and 77%. It is not necessary to hold the material for the same length of time as in the first decrystallization. In fact, this second decrystallization can be as short as the few minutes it takes to mix the acid and the solids. This second decrystallization also results in the formation of a thick gel 26.

The concentrated acid is then diluted, preferably to a concentration of between 20% and 30% and preferably using recycled water 27. The mixture is then heated to effect a second hydrolysis. The resulting gel 28 is pressed to obtain a second acid sugar stream 30, and the streams from the two hydrolysis steps are combined. The remaining lignin-rich solids are collected and optionally pelletized for fuel 29. Advantageously, pelletization of the lignin-rich cake helps reduce the waste produced by the process of the present invention.

The second decrystallization and hydrolysis steps are further explained in Examples 10 and 11 which follow.

EXAMPLE 10

The cake formed from pressing after the first hydrolysis of rice straw was collected and dried to a moisture content of 10%. The cake, containing 41% cellulose and weighing 50.03 grams, was mixed with 33.28 grams of 77% $H_2SO_4$ to achieve a ratio of pure acid to cellulose of 1.25 to 1. The cake was slowly added to the acid and mixed until a thick gel was formed. The resulting pure acid concentration in the mixture was 30.75%, thus 17.00 grams of water was added to provide a final pure acid concentration of 25.5%. The mixture was then heated at 100° C. for 50 minutes. After cooling, the gel was pressed to recover 31.45 grams of a liquid containing 18.2% sugar and 21.1% acid. The cake containing the solids remaining after pressing was washed with 25 grams of water to produce a solution which was 15.4% sugar and 19.7% acid.

The pressed cake was dried to a water content of about 10%. This cake was shown to have a fuel value of 8,600 BTU per pound. This fuel material, which is primarily lignin with unrecovered sugar, some sugar degradation products, and some unreacted cellulose burned extremely well but left an ash that contained about 7% silica.

EXAMPLE 11

The rice straw hydrolysis cake remaining after processing to remove silica, as explained in Example 7, which weighed 500 grams was mixed with 77% $H_2SO_4$ to achieve a ratio of pure acid to cellulose of 1.25 to 1. The cake was slowly added to the acid and mixed until a thick gel was formed. Water was then added to provide a final pure acid concentration of 25.5%. The mixture was then heated at 100° C. for 50 minutes. After cooling, the gel was pressed to recover a liquid containing both sugar and acid. The cake containing the solids remaining after pressing was washed with water to produce a second solution containing both sugar and acid.

The pressed cake was dried to a water content of about 10%. This cake was shown to have a fuel value of 8,600 BTU per pound. This fuel material, which is primarily lignin with unrecovered sugar, some sugar degradation products, and some unreacted cellulose burned extremely well and left an ash with a silica content of less than 1%.

Separation of Acid and Sugar

Figure 2:
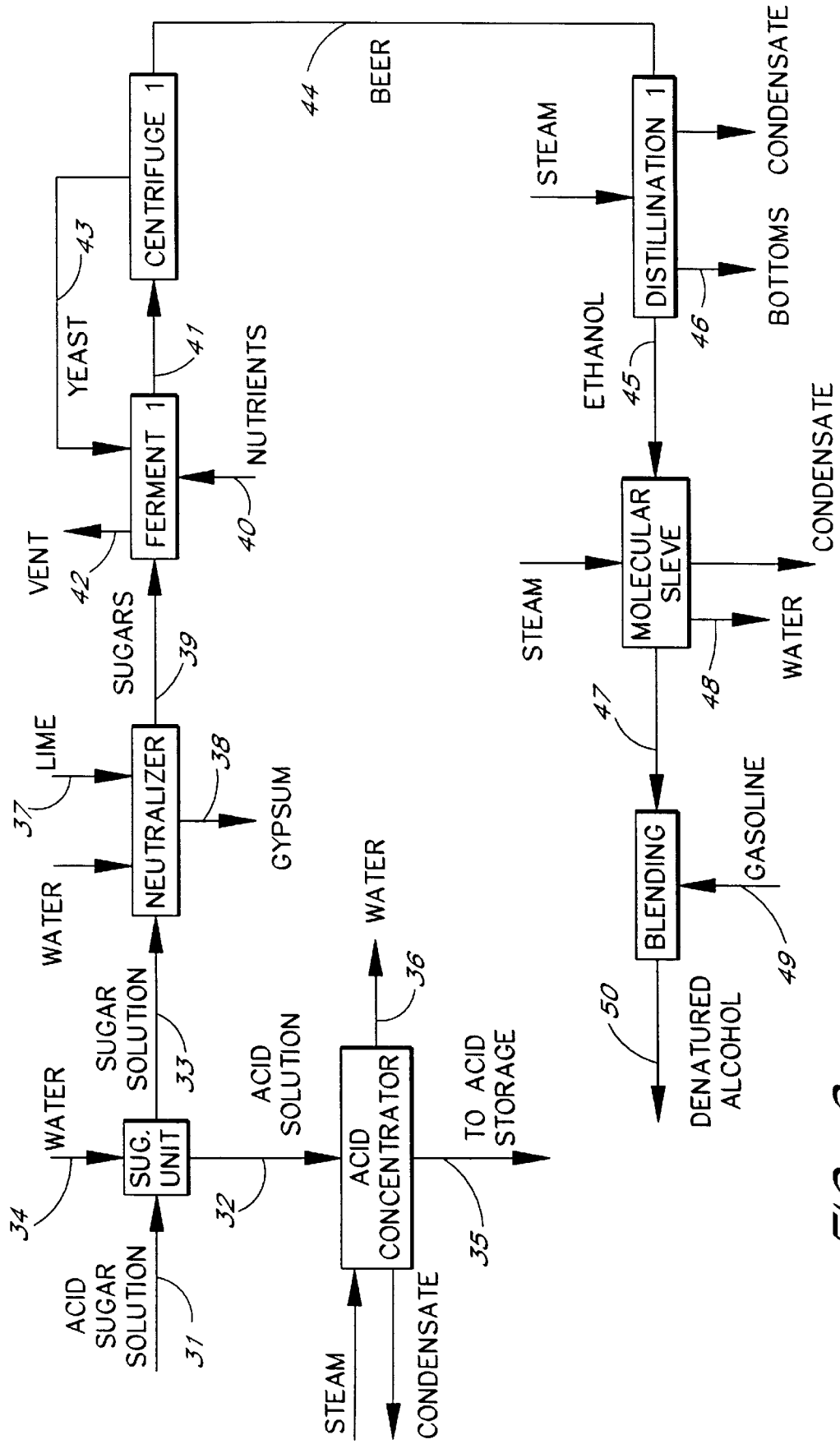
FIG. 2 is a schematic view of the method of the present invention, illustrating the separation, fermentation and acid reconcentration stages.

A further aspect of the present invention involves an improved method for separating the acid and sugar in the hydrolysate produced from the acid hydrolysis of cellulosic and hemicellulosic material. Referring now to FIG. 2, the acid sugar stream 31 is further processed through a separation unit, which comprises a strong acid polystyrenedivinylbenzene resin bed. The resin is preferably crosslinked with divinylbenzene, which is preferably at a concentration of between 6% and 8%, and treated with sulfuric acid such that it has a strong acid capacity of at least 2 meq/g. Several such resins are commercially available, including DOWEX 40166, available from Dow Chemical, Finex GS-16, available from Finex, Finland, Purolite PCR-771, available from Purolite Inc., Bala Cynwyd Pa., and IR-118, available from Rohm and Haas. In a particularly preferred embodiment, the resin used is DOW XFS 43281.01, available from Dow Chemical. The resin is preferably in the form of beads which are between 200 to 500 micrometers in diameter. The flow rate of the resin bed is preferably 2 to 5 meters per hour, and the bed preferably has a tapped bed density of between 0.6 and 0.9 g/ml. The resin bed should be heated, preferably to a temperature of between 40°–60° C. Higher temperatures can be used, but will result in premature degradation of the resin bed. Lower temperatures will result in separations which are not as effective.

The sugar is adsorbed on the column as the acid solution moves therethrough 32. Once the acid has eluted, the resin may optionally be purged with a gas which is substantially free of oxygen, preferably less than 0.1 ppm dissolved oxygen. This gas acts to push any remaining acid out of the resin, resulting in a cleaner separation.

After the elution of the acid stream, the resin is washed with water 34 that is substantially free of oxygen. The dissolved oxygen content of the water is preferably below 0.5 ppm, and more preferably, below 0.1 ppm. This washing results in the production of a sugar stream 33 containing at least 98% of the sugars in the hydrolysate that was added to the separation unit.

As a result of the separation process, three streams are collected: the acid stream, the sugar stream, and a mixed acid-sugar stream which is recycled through a second separation process. The acid stream 32 is reconcentrated and recycled for reuse, as will be explained more fully below. The sugar stream 33, which preferably contains at least 15% sugar and not more than 3% acid, can then be fermented, if desired. The purity of the sugar can be calculated as a percentage of the nonaqueous components of the sugar stream. Thus, any sugar purity of above 83.3% ($100 \times 15/18$) is suitable for fermentation.

The inclusion of acid concentration as high as 3% in the sugar stream does not cause problems for further processing. However, loss of significant proportions of sugar with the acid upon separation can decrease the overall economy of the process.

In an exemplary, ideal separation process, 100 grams of water would be used to elute a 100 gram sample solution containing 30 grams of acid, 15 grams of sugar, and 55 grams of water from a separation column. In the case of perfect separation, the sugar stream would contain 15 grams of sugar and 85 grams of water. This would leave 30 grams of acid and 70 grams (100+55−85) of water for recovery of acid in the same concentration, 30%, as the original solution.

However, a typical elution for the 100 gram sample solution referred to above would require that about 200 grams of water be added to the column. The sugar stream is still 15%, but now the acid stream contains 170 grams (200+55−85) of water and 30 grams of acid, resulting in a 15% acid concentration. Thus, if the acid stream was 95% pure with an acid concentration of 15%, approximately 1.5 grams of sugar would be lost with the acid with every elution. If the sugar stream was 95% pure at a 15% concentration, only 0.75 grams of acid would be lost with every elution. This difference is due to the fact that the acid stream contains twice as much material. Thus, the purity of the acid stream is a more important factor than the purity of the sugar stream.

The separation of the acid and sugars is further explained in Examples 12–19 which follow.

EXAMPLE 12

An acid sugar stream produced by the hydrolysis of cellulosic and hemicellulosic material was separated by flowing it through a 50 cm diameter glass column of 1.2 liters volume packed with PCR-771, a strong acid cation exchange resin available from Purolite, Inc. The column was held at 60° C. and the volumetric flow rate was 70 ml/min, which translates into a linear flow rate of about 0.8 meters per hour. Three streams were collected, the acid stream, the sugar stream and a mixed stream for recycle to another resin bed. The acid stream was 96.8% pure (sum of acid and water). The sugar stream was 86.8% pure (sum of sugar and water). Overall, the recovery of the acid was 97.3% and the recovery of the sugar was 95.5%.

EXAMPLE 13

A portion of hydrolysate liquid produced by the acid hydrolysis of cellulosic and hemicellulosic material was separated by flowing it through a 50 cm diameter glass column of 1.2 liters volume packed with PCR-771, a strong acid cation exchange resin available from Purolite, Inc. The column was held at 40° C. and the volumetric flow rate was 70 ml/min. Three streams were collected, the acid stream, the sugar stream and a mixed stream for recycle to another resin bed. The acid stream was 95.1% pure (sum of acid and water). The sugar stream was 93.1% pure (sum of sugar and water). Overall, the recovery of the acid was 98.6% and the recovery of the sugar was 90.6%.

EXAMPLE 14

A hydrolysis liquid containing 34.23% $H_2SO_4$ and 16.5% sugar was separated by flowing it through a 50 cm glass column of 1.2 liters volume packed with PCR-771, a strong acid cation exchange resin available from Purolite, Inc. The column was held at 60° C. and the volumetric flow rate was 70 ml/min. Three streams were collected, the acid stream, the sugar stream and a mixed stream for recycle to another resin bed. The acid stream was 96.47% pure (sum of acid and water). The sugar stream was 92.73% pure (sum of sugar and water). Overall, the recovery of the acid was 97.9% and the recovery of the sugar was 95.0%.

EXAMPLE 15

Hydrolysate liquid produced from the hydrolysis of newspaper was found to contain 31.56% acid and 22.97% sugar. The liquid was separated by flowing it through a 50 cm glass column of 1.2 liters volume packed with PCR-771, a strong acid cation exchange resin available from Purolite, Inc. The column was held at 40° C. and the volumetric flow rate was 70 ml/min. Three streams were collected, the acid stream, the sugar stream and a mixed stream for recycle to another resin bed. The acid stream was 96.7% pure (sum of acid and water). The sugar stream was 90.9% pure (sum of sugar and water). Overall, the recovery of the acid was 99.5% and the recovery of the sugar was 96.7%.

EXAMPLE 16

Hydrolysate liquid produced from the hydrolysis of newspaper was found to contain 31.56% acid and 22.97% sugar. A portion of the liquid was separated by flowing it through a 50 cm glass column of 1.2 liters volume packed with Finex GS-16, a strong acid cation exchange resin available from Finex, Finland. The column was held at 60° C. and the volumetric flow rate was 70 ml/min. A second portion of the liquid was also separated by flowing it through a 50 cm glass column of 1.2 liters volume packed with Finex GS-16. This column was held at 40° C. and the volumetric flow rate was 70 ml/min. In both cases, three streams were collected, the acid stream, the sugar stream and a mixed stream for recycle to another resin bed. The acid streams were at least 90% pure (sum of acid and water). The sugar streams were at least 94% pure (sum of sugar and water).

EXAMPLE 17

A hydrolysate containing 15% sugar and 30% acid was separated using a 50 cm glass column of 1.2 liters volume packed with DOW XFS 43281.01 resin, available from Dow Chemical. The column was held at 60° C. and the volumetric flow rate was 65 ml/min. After adding the hydrolysate, the column was eluted with boiled and cooled distilled water. The acid stream was 97.0% pure, and the sugar stream was 97.2% pure. The amount of swelling between the acid and water phases on the resin was 2.48%.

A second addition of the same hydrolysate to the column followed by elution recovered essentially all of the acid and sugar, with over 99.1% recovery, and 97.2% sugar purity and 92.3% acid purity. The elution rate during the separation was 65 ml/min.

EXAMPLE 18

An AST LC1000 rotating resin bed device manufactured by Advanced Separation Technologies, Inc. was used to separate the sugar-acid mixtures. The device consisted of 20 columns of resin, each column containing 2 liters of bed volume. The columns were filled with Finex GS-16 resin held at 60° C. In one run of 8 hours, the feed consisted of 14.89% sugar and 23.79% acid. The elution rate was 244 ml/min, which corresponds to linear rate of 0.12 m/min or 7.3 m/hour. The sugar product purity was 94.6% and the acid product purity was 92.4%. The sugar recovery was 84% with a concentration of 13.9%. The acid recovery was 97.5% with a concentration of 7.5%.

EXAMPLE 19

An AST LC1000 rotating resin bed device manufactured by Advanced Separation Technologies, Inc. with a total bed volume of 15.2 liters was used to separate the sugar-acid mixtures. The columns were filled with Purolite PCR-771. The feed contained 12.6% sugar and 18.9% acid. The elution flow rate was 117 ml/min. The sugar purity in the recovered stream was 92.4% and the acid purity was 92.1% when the columns were operated at 60° C.

Concentration and Recycling of Acid

The acid solution 32 recovered from the separation unit can be concentrated and recycled for reuse in the earlier stages of the process of the present invention. Concentration of the acid up to 35% is achieved through the use of a standard single stage evaporator 36. A triple effect evaporator available from Chemitrix, Toronto, Ontario, Canada, is preferably used, resulting in increased concentrations of 70–77%. The water 35 recovered in the concentrator can be used as elution water in the resin separator unit.

Fermentation

Another aspect of the present invention involves an improved method for fermenting the sugar stream separated after the acid hydrolysis of cellulosic and hemicellulosic materials. The sugar stream contains both hexose and pentose sugars. These sugars can optionally be fermented simultaneously using naturally occurring microorganisms. Advantageously, this obviates the need for separation of the sugars, or their sequential fermentation.

The sugar solution 33 recovered from the separation unit after acid hydrolysis may still contain a residual amount of acid. This acid should first be neutralized 37, preferably with slaked lime, to a pH of between 10 and 12. This high pH advantageously removes all traces of metal ions that might interfere with subsequent processing. Nutrients 40 such as magnesium, nitrogen, potassium phosphate and vitamins are then added to facilitate the growth of microorganisms.

One important aspect of the present invention is the ability to ferment both $C_5$ and $C_6$ sugars 39 together when desired. We have discovered that certain yeasts 43 cultured in a certain way are effective in this double fermentation. We have found that Candida kefyr, Pichia stipitis, and respiratory deficient strains of Saccharomyces cerevisiae, among others, work well at 25°–32° C., provided that they have been previously grown on pentose solutions for 1–2 weeks before being used on the mixed sugars.

If one desires to ferment the hexoses separately to recover the pentoses for other purposes, one can use known glucose yeasts such as Saccharomyces cerevisiae, Kluveromyces shehatae (var. shehatae, licnosa and insectosa. Certain bacteria also produce useful fermentation products and can be used in connection with the method of the present invention. The bacteria include Clostridium species and Zymomonas mobilis.

In cases where the yeast or bacterial fermentations slow down due to the repressing effects of ethanol or other volatile products, the volatile fermentation products can be removed continuously by recirculating the carbon dioxide produced by the fermentations through a cooled condensing column and then reintroducing the carbon dioxide into the fermenter. The volatile components, along with some water, condense in the column and can be collected for further purification. The process also has the advantageous effect of cooling the fermenter which is required for very active fermentations.

After the fermentation is complete, which takes approximately 3–5 days, the fermentation products and microorganisms are separated, preferably by centrifugation 41. The microorganisms 43 can be recycled to the next batch of sugars. The alcohol solution 44 can be sent to a distillation column 46 for further processing.

The preferred method of fermentation is further explained in Examples 20–21 which follow.

EXAMPLE 20

Sugar solutions obtained from the resin separation columns over several runs were combined and neutralized with $Ca(OH)_2$ to pH 10 to 11. The solution was filtered to separate $CaSO_4$ (gypsum) and a clear yellowish sugar liquid. The pH of the sugar liquid was adjusted down to pH 4.5 by use of a combination of concentrated phosphoric acid and sulfuric acid. Phosphoric acid was added first to deliver 0.3 g/l of $H_3PO_4$. Nutrients were then added before the neutralization while the solution is still sterile due to the high pH. The nutrients included 0.07 g/l of $MgSO_4$, 0.2 g/l of $KNO_3$, 0.5 g/l of urea, 1.0 g/l of yeast extract, 0.1 mg/l of FeNaEDTA, 0.01 mg/l of $H_3BO_3$, 0.04 mg/l of $MnSO_4 \cdot H_2O$, 0.02 mg/l of $ZnSO_4 \cdot 7H_2O$, 0.003 g/l KI, 1 µg/l of $Na_2MoO_4 \cdot 2H_2O$, 0.1 µg/l of $CuSO_4 \cdot 5H_2O$ and 0.1 µg/l of $CoCl_2 \cdot 6H_2O$.

The solution was then fed into a fermenter containing Candida kefyr (ATCC 8619), Pichia stiitis (NRRL Y-7124), Hansenula anomala (ATCC 42398), Hansenula anomala (ATCC 8168), Hansenula fabianii (ATCC 16755), Hansenula jadinii (ATCC 18201), or a respiratory deficient strain of Saccharomyces cerevisiae, which had been previously grown on 5% xylose media. The yeast "cream" in the fermenter contains at least 20 grams of yeast in approximately 100 ml of the 2 liter fermenter volume. Approximately 200 ml of the solution is added. The addition was repeated each day for three days. The yeast fermented both the C6 and C5 sugars in the solution.

EXAMPLE 21

Sugar solutions obtained from the resin columns were combined and neutralized with $Ca(OH)_2$ to pH 10 to 11. The solution was filtered to separate $CaSO_4$ (gypsum) and a clear yellowish sugar liquid. The pH of the sugar liquid was adjusted down to pH 4.5 by use of a combination of concentrated phosphoric acid and sulfuric acid. Phosphoric acid is added first to deliver 0.35 g/l of $H_3PO_4$. Nutrients are added before the neutralization while the solution is still sterile due to the high pH. The nutrients included 0.07 g/l of $MgSO_4$, 0.2 g/l of $KNO_3$, 1.0 G/L OF $(NH_4)_2SO_4$, 1.0 g/l of yeast extract, 5.0 mg/l of $FeSO_4$, 1.0 mg/l of $H_3BO_3$, 5.0 mg/l of $MnSO_4 \cdot 2H_2O$, 10 µg/l of $CuSO_4 \cdot 4H_2O$, 20 µg/l of $CoCl_2 \cdot 6H_2O$, 10 µg/l biotin, 0.25 mg/l pyridoxine HCl, 1.5 mg/l i-inositol, 2.0 mg/l Ca pantothenate, 5.0 mg/l thiamine HCl and 25 mg/l of peptone.

The solution was then fed into a fermenter containing Candida kefyr (ATCC 8619), Pichia stipitis (NRRL Y-7124), Hansenula anomala (ATCC 42398), Hansenula anomala (ATCC 8168), Hansenula fabianii (ATCC 16755), Hansenula jadinii (ATCC 18201), or a respiratory deficient strain of Saccharomyces cerevisiae, which had been previously grown on 5% xylose media. The yeast "cream," estimated to contain at least 20 grams of yeast, occupied approximately 100 ml of the 2 liter fermenter. Approximately 200 ml of the solution is added. The addition was repeated each day for three days. The yeast fermented both the C6 and C6 sugars in the solution.

The addition of $H_3BO_3$ to the media can be eliminated, if desired. $H_3BO_3$ should not be added to the media if bacteria, rather than yeasts, are used for fermentation, since boron is toxic to the bacteria.

Although certain examples have been used to illustrate and describe the present invention, it is intended that the scope of the invention not be limited to the specific examples set forth herein. Accordingly, the scope of the invention is intended to be defined only by the claims which follow.

What is claimed is:

1. A method of separating acid and sugars from liquids resulting from the acid hydrolysis of materials containing cellulose and hemicellulose, comprising:

adding the liquids to a resin separation unit comprising a cross linked polystyrene ion exchange resin bed whereby the sugar is adsorbed on the resin, thereby producing an acid stream containing less than 2% sugar.

2. The method of claim 1, wherein said resin is cross linked with divinylbenzene and treated with sulfuric acid to produce a strong acid resin.

3. The method of claim 2, wherein the divinylbenzene is at a concentration of from about 6% to about 8%.

4. The method of claim 1, wherein said resin is made by polymerizing vinylbenzyl chloride with divinylbenzene and treating with sodium sulfite.

5. The method of claim 4, wherein the divinylbenzene is at a concentration of from about 6% to about 8%.

6. The method of claim 1, wherein said resin is in the form of beads having a diameter of from about 200 to about 500 micrometers.

7. The method of claim 1, wherein liquid flows through the resin bed with an average linear flow rate of from about 2 to about 5 meters per hour.

8. The method of claim 1, further comprising heating said resin bed to a temperature of from about 40 to about 60 degrees Celsius.

9. The method of claim 1, wherein the resin has a strong acid capacity of at least about 2 meq/g.

10. The method of claim 1, wherein the resin bed has a tapped bed density of from about 0.6 g/ml to about 0.9 g/ml.

11. The method of claim 1, further comprising washing said resin with water substantially free of oxygen, thereby producing a sugar stream containing at least 98% of the sugar in the liquid added to the separation unit.

12. The method of claim 11, further comprising purging the resin with a gas substantially free of oxygen, thereby pushing the acid out of the resin before the washing step.

* * * * *